United States Patent [19]
Block et al.

[11] Patent Number: 6,037,351
[45] Date of Patent: Mar. 14, 2000

[54] METHOD OF INHIBITING HEPATITIS B VIRUS

[75] Inventors: Timothy M. Block, Jenkintown; Baruch S. Blumberg, Philadelphia, both of Pa.; Raymond A. Dwek, Oxford, United Kingdom

[73] Assignee: G. D. Searle & Co., Chicago, Ill.

[21] Appl. No.: 08/676,153

[22] PCT Filed: Dec. 23, 1994

[86] PCT No.: PCT/US94/14548

§ 371 Date: Jul. 11, 1996

§ 102(e) Date: Jul. 11, 1996

[87] PCT Pub. No.: WO95/19172

PCT Pub. Date: Jul. 20, 1995

Related U.S. Application Data

[63] Continuation-in-part of application No. 08/181,519, Jan. 13, 1994, abandoned.

[51] Int. Cl.[7] .................................................. A61K 31/445
[52] U.S. Cl. ................................................................ 514/315
[58] Field of Search ............................................... 514/315

[56] References Cited

U.S. PATENT DOCUMENTS

| | | | |
|---|---|---|---|
| 4,182,767 | 1/1980 | Murai et al. | 424/267 |
| 4,849,430 | 7/1989 | Fleet et al. | 514/315 |
| 4,957,926 | 9/1990 | Jacob et al. | 514/315 |
| 5,030,638 | 7/1991 | Partis et al. | 514/315 |

OTHER PUBLICATIONS

Gerlich and Bruss, in Hepatitis B vaccines in Clinical Practice, ed. R.W. Ellis, Marcel Dekker, Inc., pp. 41–82, 1992.

Karpas et al., Proc. Natl. Acad. Sci. USA 85, pp. 9229–9233, 1988.

Repp et al., J. Biol. Chem. 260, pp. 15673–15679, 1985.

Datema et al., Pharmac. Ther. 33, 221, pp. 259–260, 1987.

Pizer et al., J. Virol. 34, pp. 142–153, 1980.

Sells et al., Proc. Natl. Acad. Sci. USA 84, pp. 1005–1009, 1987.

Gripon et al., Mol. Biol. HBv. San Diego, CA, Abst. 67, 1992.

Heerman et al., in Viral Hepatitis and Liver Disease, ed. Zuckerman A.R. Liss, pp. 697–700, 1988.

Heeman et al., J. Virol. 52, pp. 396–402, 1994.

Block et al., Proc. Natl. Acad. Sci. USA 91, 2235–2239 (1994).

Ganem, Chemtracts: Organic Chem.—7(2), 106–107 (1994).

Repp et al., J. Biol. Chem. 260, 15873–15879 (1985).

Niemann et al., Hoppe–Seyler's Zeitschrift Physiol. Chem.—365, p. 1040 (1984).

Kasambalides et al., J. Gen. Virol. 66, 2443–2451 (1985).

Karlsson et al., J. Biol. Chem.—268, 570–576 (1993).

Karpas et al., Proc. Natl. Acad. Sci. USA 85, 9229–9233 (1988).

Fleet et al., FEBS Lett. 237, 128–132 (1988).

Primary Examiner—Raymond Henley, III
Attorney, Agent, or Firm—Scott J. Meyer

[57] ABSTRACT

A method is disclosed for the treatment of hepatitis B virus (HBV) infections which comprises administering to the infected host an N-alkyl derivative of 1,5-dideoxy-1,5-imino-D-glucitol in which the alkyl group contains from 3 to 6 carbon atoms.

3 Claims, 7 Drawing Sheets

METHOD OF INHIBITING HEPATITIS B VIRUS

CROSS-REFERENCE TO RELATED APPLICATION

This is a 371 OF PCT/US94/14548 filed Dec. 23, 1994 which is a continuation-in-part of application Ser. No. 08/181,519, filed Jan. 13, 1994 now abandoned.

BACKGROUND OF THE INVENTION

This invention relates to a novel method of inhibiting hepatitis B virus and, more particularly, to the use of N-alkyl derivatives of 1,5-dideoxy-1,5-imino-D-glucitol for inhibiting replication and secretion of hepatitis B virus in cells infected with said virus.

Hepatitis B Virus (HBV) is a causative agent of acute and chronic liver disease [Ayoola et al., *Bull. World Health Organ.* 66, 443–455 (1988)]. Although effective vaccination is available [two HBV vaccines currently available are Merck's Recombivax HB and SmithKline Beecham's Engerix-B], there are still more than 300 million people worldwide chronically infected with the virus [Eder et al., in *Progress in Liver Diseases*, eds. Popper and Schaffner (Grune & Stratton, Orlando, FL), vol. 8, pp. 367–394 (1986)]. For them, the vaccine has no therapeutic value. According to Dr. Richard Duma, executive director of the National Foundation for Infectious Diseases, an estimated 300,000 cases of HBV infection occur annually in the United States alone [*Med. World News* 34(8), 20–21 (1993)]. Between 25 to 40% of those who are chronically infected with HBV develop serious liver disease. It is therefore important to find effective anti-HBV therapies.

Alpha interferon has been used for treatment of HBV infection with promising results in some patients [Hoofnagle and Jones, *Seminars in Liver Disease* 9, 231–233 (1989); and Perrillo, *Seminars in Liver Disease* 9, 240–248 (1989)]. The only treatment for chronic HBV infection currently approved by the U.S. FDA is recombinant interferon alfa-2b (Intron A, Schering-Plough). Clinical tests on the use of the nucleoside analog, fialuridine, for treatment of chronic hepatitis B were suspended recently due to drug-related liver failure in six of 20 patients. Consequently, there is a great need for a safe drug treatment of hepatitis B.

Recent reports suggest that the virus encoded DNA polymerase, which functions as a reverse transcriptase, is an attractive target [Doong et al., *Proc. Natl. Acad. Sci. USA* 88, 8495–8499 (1991); Lee et al., *Antimicrob. Aaent Chem.* 33, 336–339 (1989); Price et al., *Proc. Natl. Acad. Sci. USA* 86, 8541–8544 (1989); and Venkateswaran et al., *Proc. Natl. Acad. Sci. USA* 84, 274–278 (1987)].

Other virus-mediated processes have not been targeted for anti-viral intervention. Effective antiviral therapy for HBV is likely to involve multiple strategies, including agents that influence the host immune system as well as those that interfere with different steps in the life cycle of the virus. It is therefore of interest to explore the possibility that other, non-polymerase mediated steps in the virus life cycle are vulnerable to intervention.

1,5-Dideoxy-1,5-imino-D-glucitol (which is also known as 1-deoxynojirimycin or DNJ) and its N-alkyl derivatives are known inhibitors of the N-linked oligosaccharide processing enzymes, α-glucosidase I and II. Saunier et al., *J. Biol. Chem.* 257, 14155–14161 (1982); Elbein, *Ann. Rev. Biochem.* 56, 497–534 (1987). As glucose analogs they also have potential to inhibit glucosyl-transferases. Newbrun et al., *Arch. Oral Biol.* 28, 516–536 (1983); Wang et al., *Tetrahedron Lett.* 34, 403–406 (1993). Their inhibitory activity against the glucosidases has led to the development of these compounds as antihyperglycemic agents and anti-viral agents. See, e.g., PCT Int'l. Appln. WO 87/03903 and U.S. Pat. Nos.: 4,065,562; 4,182,767; 4,533,668; 4,639,436; 4,849,430; 4,957,926; 5,011,829; and 5,030,638.

Studies on the effect of inhibitory agents on hepatitis B virus (HBV) have been sparse heretofore due to the lack of permissive cell culture systems for assay purposes. That is, the inability heretofore to reproduce and productively infect tissue cultures with the virus has been a serious limitation to the discovery of useful anti-HBV agents.

In one study, N-methyl deoxynojirimycin has been reported to inhibit the formation of mouse hepatitis virus (MHV) whereby the appearance of E2 on the cell surface is delayed. See Repp et al., *J. Biol. Chem.* 280, 15873–15879 (1985); Datema et al., *Pharmac. Ther.* 33, 221–286, at 260 (1987). However, MHV is unrelated to the hepatitis B virus (HBV). On the one hand, HBV is a member of the Hepadnavirus family and is a small virus pathogen in humans. The HBV size is approximately 42 nM with a DNA genome size of 3.5 kb.

On the other hand, MHV is a member of the Coronavirus family, and is a large RNA-containing virus that is not pathogenic to humans, although human coronavirus pathogens that cause upper respiratory tract infections are common. The MHV size is about 100–150 nM (being rather pleiotropic), with an RNA genome size of approximately 30 kb. There are very few similarities between HBV and MHV. Further background information and a complete description of Coronaviruses (including MHV) can be had by reference to K. Holmes, in *Virology*, 2d edition, ed. by B. Fields, pp. 841–856, Raven Press, New York, N.Y., 1990.

The inability to predict the results from one virus to another is evident from the recent reports by two different scientific groups that hepatitis delta virus (HDV) secretion was not dependent upon HBV sAg glycosylation. W. Hui-Lin et al., Abstr. 115, and C. Gureau et al., Abstr. 117, in Abstracts of Papers Presented at the 1994 Meeting, "Molecular Biology of Hepatitis B Viruses," Oct. 3–6, 1994, Institut Pasteur, Paris, France.

HDV does not specify its own envelope protein. It infects the same cells as HBV, and uses the HBV S antigen (HBV envelope protein) to make the infectious, mature HDV particle. By way of distinction, HBV secretion is dependent upon glycosylation and glycan trimming. That is, although HBV and HDV are composed of the same envelope proteins, HDV secretion is glycosylation independent whereas HBV is very sensitive to glycosylation.

The effect of the glycosylation inhibitor, tunicamycin, on hepatitis B virus cell culture systems has been described by Pizer et al., *J. Virol.* 34, 134–153 (1980); Datema et al., supra at 270. However, tunicamycin undesirably and completely prevents the addition of N-linked oligosaccharides to newly synthesized polypeptide. That is, treatment with tunicamycin results in complete inhibition of N-linked glycosylation of proteins and is very toxic to cells. Moreover, tunicamycin treatment of HBV infected cells resulted in no significant reduction of HBV secretion.

BRIEF DESCRIPTION OF THE INVENTION

In accordance with the present invention a method is provided for inhibiting hepatitis B virus (HBV) in cells infected with said virus. The method comprises treatment of said cells with an N-alkyl derivative of 1,5-dideoxy-1,5- imino-D-glucitol in which said alkyl group contains from 3 to 6 carbon atoms in an effective amount to inhibit replication and secretion of HBV virions. The N-alkyl group preferably is butyl.

In a preferred illustrative example of the invention, N-butyl-1,5-dideoxy-1,5-imino-D-glucitol (NB-DNJ) is shown to suppress the secretion of HBV particles and to cause intracellular retention of HBV DNA in both stably transfected HepG 2.2.15 cells and HBV infected HepG2 cells.

HepG2 cells are well-known, widely distributed, and readily available human hepatoma cells. The establishment and characteristics of the HepG2 cell line are described in U.S. Pat. No. 4,393,133. Samples of this cell line are also available from the American Type Culture Collection, Rockville, Maryland, under accession number ATCC HB 8065, and from the European Collection of Animal Cell Cultures, Porton Down, UK. These cells have been used as a source of various proteins, e.g., tissue factor inhibitor (TFI), also known as lipoprotein associated coagulation inhibitor (LACI), by Broze and Miletich, *Proc. Natl. Acad. Sci. USA* 84, 1886–1890 (1987), and in U.S. Pat. Nos. 4,996,852, 5,106,833 and 5,212,091.

HepG 2.2.15 cells are derivatives of HepG2 cells and are prepared as described by Sells et al., *Proc. Nat'l. Acad. Sci. USA* 84, 1005–1009(1987).

The suppression of the secretion of HBV particles by the method of the invention was most unexpected since it has been previously reported that tunicamycin treatment of HBV-producing cells resulted in normal HBV particle secretion. See Grippon et al., *Mol. Biol. HBV*, San Diego, Calif., Abstract page 67 (1992). It has been found by the present inventors that secretion of HBV virions but not subviral particles is inhibited by tunicamycin.

The increase in intracellular HBV DNA resulting from treatment by the method of the invention was also unexpected.

Since HBV envelope proteins contain only one or two N-linked glycans per molecule, the ability to inhibit secretion of such modestly (by weight) glycosylated proteins and their virion products by the N-alkyl derivatives of DNJ was surprising when contrasted to their lesser effect upon the secretion of HIV which contains heavily glycosylated envelope proteins. It was also unexpected to find that HBV virions and particles containing large cocarboxy- terminal proteins, LHBs, and middle MHBs were more sensitive to N-butyl DNJ than were small SHBs enriched particles.

Another of the advantages in the use of the defined N-alkyl derivatives of DNJ is their relative non-toxicity. For example, the N-butyl derivative is known to be non-toxic ($TD_{50}$>5 mM) at its effective concentration for inhibition of HIV replication $EC_{50}$=43 $\mu$M). See, e.g., Bryant et al., Abstracts of 10th International Conference on AIDS, Berlin, Jun. 7–11, 1993. It is also shown herein that 90% of HepG 2.2.15 cells infected with HBV and treated with 1000 $\mu$g/ml of the N-butyl derivative of DNJ were as viable as untreated controls.

In view of the results demonstrated herein, it is believed that other compounds that inhibit transport of HBV virions or steps in the glycosylation trimming pathway will be useful in inhibiting HBV morphogenesis in tissue culture and mammalian hosts.

DETAILED DESCRIPTION OF THE INVENTION

While the specification concludes with claims particularly pointing out and distinctly claiming the subject matter regarded as forming the invention, it is believed that the invention will be better understood from the following illustrative detailed description taken in conjunction with the accompanying drawings in which:

FIG. 2 in two parts, FIGS. 2A and 2B, shows autoradiograms of HBV DNA in the media and cells of cultures treated with N-butyldeoxynojirimycin (NBDNJ). HepG 2.2.15 cells were grown for 6 days in the presence of the indicated concentration of NBDNJ with one change of medium. After the sixth day (seventh day in culture), cells and medium were collected. Autoradiograms of the viral DNA detected by hybridization of membranes to HBV probes are shown.

lane 2: 200 $\mu$g/ml;

lane 3: 500 $\mu$g/ml;

lane 4: 1000 $\mu$g/ml.

Lane 5: EcoRI digested DNA isolated from virions prepared from untreated 2.2.15 cells.

Lane 6: plasmid DNA as a hybridization control. Arrows: indicate the expected mobility for relaxed circular HBV genomes (A) and linearized 3.2 kb genomes (B).

FIG. 3 in four parts, FIGS. 3A, 3B, 3C and 3D, shows gel electrophoresis and histograms of HBV DNA in the cells and medium of HepG2 cells infected with HBV and treated with NBDNJ.

Lane 1: molecular weight markers;

Lane 2: Blank;

Lane 3: Medium from cells that received no NBDNJ;

Lanes 4 and 5: medium from cells that received 200 $\mu$g/ml NBDNJ;

Lanes 6 and 7: 500 $\mu$g/ml NBDNJ;

Lanes 8 and 9: 700 $\mu$g/ml NBDNJ, 10 and 11: 1000 $\mu$g/ml NBDNJ.

These bands were imaged by densitometry and the areas under the peaks are shown in FIG. 3C in which the average of the two samples of each NBDNJ concentration was plotted.

FIG. 3B and FIG. 3D: DNA from the intracellular compartment of the cultures infected in FIG. 3A with HBV and treated with NBDNJ were amplified by PCR. The lanes contain amplified DNA from the following samples:

Lanes 1 and 2: No NBDNJ;
Lanes 3 and 4: 200 μg/ml NBDNJ;
Lanes 5 and 6: 500 μg/ml NBDNJ;
Lanes 7 and 8: 700 μg/ml. NBDNJ;
Lanes 9 and 10: 1000 μg/ml. NBDNJ.

FIG. 4 in six parts.

For comparison, 2.28 mM approximately equals 500 μg/ml of NBDNJ. The Y axis shows the calorimetric signal of the ELISA reaction, in arbitrary OD units, read by the plate reader.

FIG. 5 in three parts.

Lanes are as indicated at the top of each part of FIG. 5. 1.0 μg of HBV genotype D, purified from human serum is used as a control.

Molecular weight markers (mw) in kilodaltons (kd) are shown at the right side of each part of FIG. 5.

Arrows at the left show LHBs (S1) and MHBs (S2) polypeptides.

Figure 1:
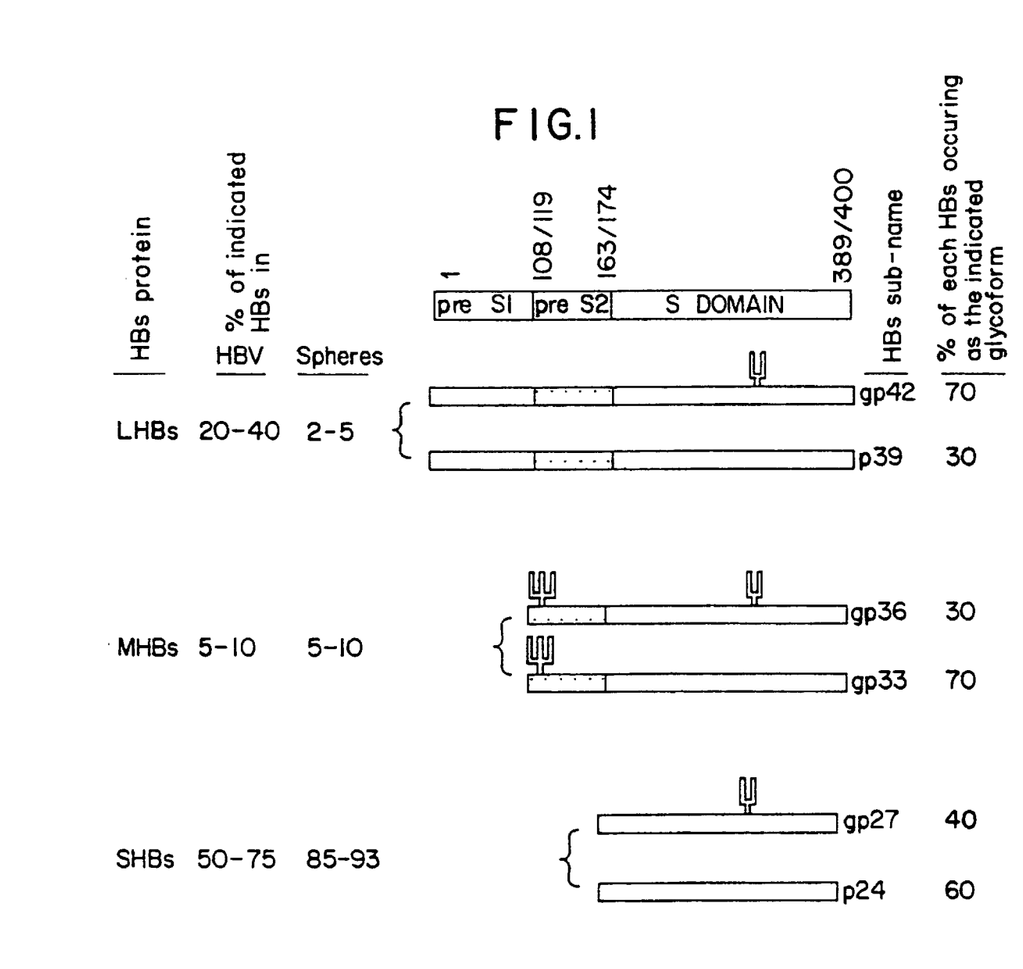
FIG. 1 shows the genetic map of HBV envelope proteins. The upper-most line shows a linear map of the HBs genes, with the preS1, preS2 and S domains indicated. Numbers under this map indicate the boundaries of the domains, expressed as amino acid number. The numbers vary for different HBV strains. The percentage values in the right-hand column show the fraction of non-, mono-, and di-glycosylated proteins for each HBs. Values are from Gerlich and Bruss, in *Molecular Biology of HeDatitis B Virus*, ed. A. McLachlan, CRC Press, pp. 109–144 (1992), and in *Hepatitis B Vaccines in Clinical Practice*, ed. R. W. Ellis, Marcel Dekker, Inc., pp. 41–82 (1992).

The HBV envelope contains three co-carboxy-terminal proteins (HBs), termed large (LHBs), middle (MHBs) and small (SHBs) protein (see FIG. 1). These proteins result from the alternate translation initiation of a single open reading frame (ORF) [Ganem, in *Hepadnaviruses*, eds. Mason and Seeger (Springer-Verlag), pp. 61–84 (1991)]. All three HBs proteins occur with complex type N-linked oligosaccharides at amino acid 146 of the S domain [see FIG. 1 and Gerlich and Bruss, in *Molecular Biology of Hepatitis B Virus*, ed. A. McLachlan, CRC Press, pp. 109–144 (1992), and in *Hepatitis B Vaccines in Clinical Practice*, ed. R. W. Ellis, Marcel Decker, Inc., pp. 41–82 (1992)].

MHBs (but never LHBs) also occurs with hybrid type oligosaccharides within the preS2 domain. During natural infection with HBV, the liver produces a large excess of HBs proteins which are secreted as either filamentous or spherical sub-viral particles of 20 nM in diameter [Ganem, in *Hepadnaviruses*, pp. 61–84 (1991); and Gerlich and Bruss, in *Molecular Biology of Hepatitis B Virus*, and in *Hepatitis B Vaccines in Clinical Practice*, supra.] HBs spheres are most abundant and contain five to ten times less LHBs than do HBs filaments and HBV particles. MHBs is a minor component of all three types of particles [Gerlich and Bruss, in *Molecular Biology of Hepatitis B Virus*, and in *Hepatitis B Vaccines in Clinical Practice*, supra.]

The morphoaenesis of HBV is complex. Preassembled viral core particles are believed to attach to the cytosolic sides of viral envelope (surface) proteins, which have inserted into the endoplasmic reticulum (ER) membrane [Gerlich and Bruss, in *Molecular Biology of Hepatitis B Virus*, and in *Hepatitis B Vaccines in Clinical Practice*, supra.]

After acquiring envelopes, virions bud to the lumen of the ER, from where they are transported through the Golgi apparatus into the extracellular fluid. Immature glycoproteins contain three terminal glucose residues on the N-linked oligosaccharides.

The removal of terminal glucose residues is thought to play an important role in the migration of immature glycoproteins from the ER to the Golgi [Datema and Romero, *Pharmacol. Thera.* 33, 221–286 (1987)]. The imino sugar, NBDNJ, is a potent inhibitor of α-glucosidase I, a cellular enzyme which removes terminal glucose residues from nascent oligosaccharides, and has been found to suppress formation of cytotoxic Human Immunodeficiency Virus (HIV) in vitro [Karpas et al, *Proc. Natl. Acad. Sci. USA* 85, 9229–9233 (1988); U.S. Pat. No. 4,849,430; and Walker et al., *Proc. Natl. Acad. Sci. USA* 84, 8120–8124 (1987). Since HBV secretion requires LHBs and SHBs, both of which bear N-linked oligosaccharides, the effect of NBDNJ upon virus synthesis was tested.

In order to further illustrate the invention, the following detailed examples were carried out although it will be understood that the invention is not limited to these specific examples or the details described therein.

EXAMPLES

METHODS

Cells and media:

HepG2 cells were purchased from the European Collection of Animal Cell Cultures (Porton Down, UK). HepG2 2.15 [2.2.15, Sells and Chen, *Proc. Natl. Acad. Sci. USA* 84, 1005–1009 (1987)] cells were obtained from Dr. George Acs (Mt. Sinai Medical College, New York, USA).

All tissue cultures were maintained in 5% $CO_2$ in RPMI 1640 (GIBCO) medium, supplemented with 10% heat inactivated fetal calf serum (Techgen, London, U.K.), 50 units/ml. of penicillin and streptomycin, 1 mM glutamine (GIBCO). For 2.2.15 cells, 200 μgs/ml. Antibiotic G418 (Genticin, GIBCO) was added to the medium, as in Sells and Chen, *Proc. Natl. Acad. Sci. USA* 84, 1005–1009 (1987).

Cell viability was measured by flow cytometry using a FACscan cytometer, Becton Dickinson, Sunnyvale, Calif., USA, after incubation with propidium iodide, as in Platt and Jacob, *Eur. J. Biochem.* 208, 187–193 (1992).

Infection of HepG2 cells:

HBV was purified from human serum or from the medium of cultured cells by sedimentation to between 40 and 46% sucrose (w/w) following ultracentrifugation, [Seifer et al., *Virol.* 179, 300–311 (1990)]. Virions were dialyzed in 0.02 M Potassium Phosphate Buffer, pH 7.4, concentrated, treated with V8 protease (from *Staphylococcus aureus*, Sigma Chemical Co.) overnight at 37° C. centrifuged for 8 hours through a 20% sucrose/0.01M Tris, pH 7.4, 0.14 M NaCl, 0.005 M EDTA (TNE) cushion. The pellets were re-suspended in growth medium and then used to inoculate HepG2 cells.

Iminosugar compounds.

The synthesis of NBDNJ is well-known and is described by Fleet et al, *FEBS Letters* 237, 128–132 (1988). NBDNJ was provided by G. D. Searle/Monsanto Co. as compound SC-48334.

Detection of viral DNA.

Medium from approximately 5×10⁶ cells was precipitated with polyethylene glycol (PEG) 8000 (Sigma), after clarification, as in Sells and Chen, *Proc. Natl. Acad. Sci. USA* 84, 1005–1009 (1987), re-suspended in 0.5 ml. phosphate buffered saline (PBS) and sedimented through a cushion of 20% sucrose in PBS for 5 hours at 50,000 rpm in a Beckman T100.3 rotor (approx. 75,000×g).

DNA was prepared from the pellets as in Sells and Chen, *Proc. Natl. Acad. Sci. USA* 84, 1005–1009 (1987). For Southern blots [Maniatis et al., *Molecular cloning, a laboratory manual*, Cold Spring Harbor Laboratory, Cold Spring Harbor, N.Y. (1982)], DNA was resolved by electrophoresis through 1.2% agarose, transferred to H+ bond (Amersham) filter paper and hybridized with radioactive $^{32}P$ (Amersham) HBV probe (made by the random priming method described by the kit manufacturer, (Amersham), using pHBV as template [Foster et al., *Proc. Natl. Acad. Sci. USA* 88, 2888–2892 (1991)].

Progeny virus in the medium of HepG2 cells infected with serum derived HBV was detected by precipitating medium with monoclonal antibody to the PreS2 epitopes. DNA from immunoprecipitated virions was amplified by a polymerase chain reaction (PCR) using primers from nucleotides 2815 and 190 with respect to the viral genome (using the EcoRI site as nucleotide 1). DNA was prepared from cell lysates by standard methods as described by [Maniatis et al., *Molecular cloning, a laboratory manual*, Cold Spring Harbor Laboratory, Cold Spring Harbor, N.Y. (1982)].

Detection of HBV proteins by the Enzyme Linked Immunoabsorbant assay (ELISA).

Monoclonal antibodies used herein are well-known and are described by Heerman et al., *J. Virol.* 52, 396–402 (1984), for antibody to PreS1 (MA 18/7); Heerman et al., *Intervirology* 28: 14–21 (1987), for antibody to PreS2 (Q 19/10), see also Gerlich and Bruss, *Molecular Biology of Hepatitis B Virus*, ed. A. McLachlan, CRC Press, 109–144 (1992), and in *Hepatitis B Vaccines in Clinical Practice*, ed. R. W. Ellis, Marcel Dekker, Inc., pp. 41–82 (1992); and Heerman et al., in *Viral Hepatitis and Liver Disease*, ed. Zuckermann, A. R. Liss, 697–701 (1988), for antibody to S (C20-2).].

Samples were incubated in microtiter wells coated (overnight at 4° C.) with monoclonal antibodies specific for the LHBs, MHBs or SHBs epitopes and blocked with 1% BSA in PBS. After incubation with virus samples in for 1 hour (37° C.), plates were washed 4 times with PBS/0.1% Tween 20 non-ionic detergent.

Bound antigen was detected by incubation with peroxidase conjugated goat anti-HBs antibody (Behring) followed by development in orthophenylenediamine (0.33 mg/ml PBS-peroxide solution). Optical densities were read in a Behring plate reader. Tests on purified virus and total medium were conducted over a series of sample dilutions to insure proper quantification.

Western Blots:

Samples were dissolved in loading buffer, resolved by electrophoresis through 13.5% SDS polyacrylamide gels (SDS-PAGE) and transferred to PVDF (Millipore) membranes and blocked with 5% powdered milk, as in Gultekin and Heerman, *Analytical Biochem.* 172, 320–329 (1989). After incubation with primary antibody overnight at room temperature in 1% bovine serum albumin (BSA) in TNE and second antibody (peroxidase conjugated goat anti-mouse IgG serum) for 1 hour in TNE at room temperature, membranes were developed in peroxide-diaminobenzidine (Sigma) PBS, as described in the manufacturer's instructions.

RESULTS

NBDNJ reduces the amount of virion associated HBV DNA released into the media by 2.2.15 cells:

2.2.15 cells are derived from the HepG2 line and chronically secrete infectious HBV as well as sub-viral particles (HBs particles and spheres) into the culture medium [Heerman et al., *J. Virol.* 52, 396–402 (1984); and Sells et al., *Proc. Natl. Acad. Sci. USA* 84, 1005–1009 (1987)].

Figure 2A:
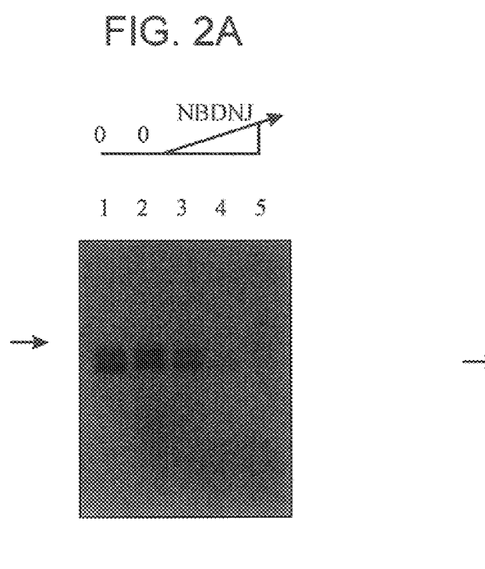
FIG. 2A: autoradiogram of a Southern blot of DNA recovered from the medium of 2.2.15 cells maintained in medium without NBDNJ (lanes 1 and 2); and in the following NBDNJ concentrations: 200 $\mu$g/ml (lane 3); 500 $\mu$g/ml (lane 4); and 1000 $\mu$g/ml (lane 5).

To determine the effect of NBDNJ upon the production and secretion of HBV, 2.2.15 cells were maintained in medium containing a range of NBDNJ concentrations for six days, with one change of medium on the third day. After six days in compound, DNA was isolated from virus (as described under "Methods" above). Viral DNA was detected by hybridization of Southern blots to radioactively labeled HBV DNA probes, as shown in FIG. 2A.

Virus-specific DNA, migrating with the expected mobility of relaxed circles and linear genome length DNA [Sells et al., *J Virol.* 62, 2836–2844 (1988)] was detected in the samples derived from untreated culture medium (lanes 1 and 2). There is a clear dose-dependent decrease in virus specific DNA obtained from the media of cells treated with NBDNJ (lanes 3, 4 and 5). The autoradiograph shown in FIG. 2A was quantified by densitometry. Densitometry revealed that 500 μg/ml (2.28 mM) and 1000 μg/ml of NBDNJ resulted in decreases of 90 and 99%, respectively.

The decrease was not due to toxicity of NBDNJ, since 90% of the cells maintained in 1000 μgs/ml NBDNJ for six days were as viable as untreated controls, as determined by FACs analysis of propidium iodide stained cells and $^{[35]}$-S methionine incorporation into proteins.

2.2.15 cells treated with NBDNJ contain elevated levels of intracellular HBV DNA.

The NBDNJ-mediated decrease in virion associated HBV DNA in the medium could have been due to a decrease in viral DNA synthesis. Alternatively, it could have been due to a post synthetic event such as virion assembly, transport or egress from the cell. To distinguish between these possibilities, the amount of intracellular HBV specific DNA in untreated and NBDNJ treated 2.2.15 cells was compared.

Figure 2B:
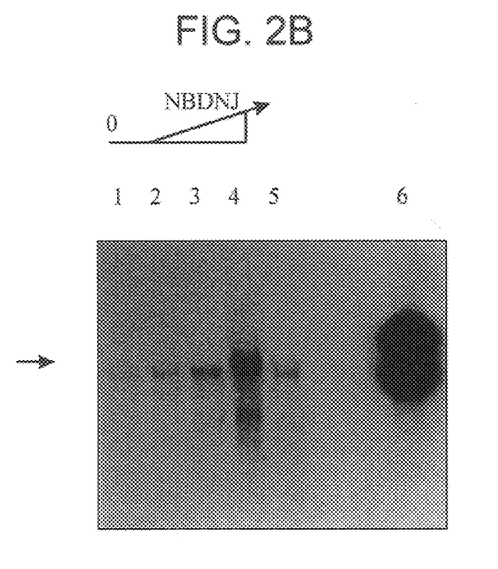
FIG. 2B: autoradiogram of a Southern blot of total intracellular DNA, digested to completion with EcoRI, from cells maintained in the absence of NBDNJ (lane 1) and in the presence of the following NBDNJ concentrations.

Total cellular DNA was prepared from treated and untreated cells and digested to completion with EcoRI to linearize viral genomes. Near equal microgram amounts of digestion products (as determined by ethidium bromide staining and hybridization to a cell specific probe) were resolved by electrophoresis, Southern blotted and hybridized with the HBV specific probe (FIG. 2B). Unit length HBV genomes migrating as 3.2 kb bands are detected in DNA derived from untreated 2.2.15 cells (lane 1) and virions isolated from control culture medium (lane 5).

Lanes 2, 3 and 4 contain DNA derived from cells treated with 200, 500 and 1000 μg/ml. NBDNJ, respectively. There is a clear dose-dependent increase in the amount of HBV DNA present in NBDNJ treated cells, as compared with untreated cells. Densitometry of this autoradiogram suggests that cells treated with 200, 500 and 1000 μgs/ml. of NBDNJ exhibit an 1.7, 3.0, 5.1 fold increase in HBV copy abundance, respectively, when adjusted for loading variation, using hybridization to a cellular MHC class III gene, G1, as a loading control.

HepG2 cells infected with HBV and treated with NBDNJ release less progeny virus.

2.2.15 cells are a useful system to study HBV production in a stably transfected environment. However, HBV pregenome synthesis, in these cells, may occur from integrated viral DNA templates and not covalently closed circular viral DNA templates, as is thought to occur during natural infection [Sells et al., *J. Virol.* 62, 2836–2844 (1988)]. Moreover, these cells produce naked core particles as well as a variety of subgenomic viral DNA products which are released in to the medium [Sells et al., supra].

Figure 3A:
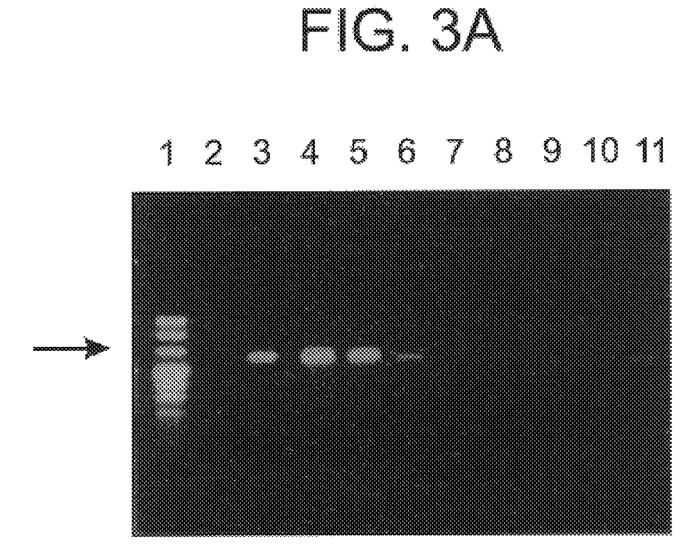
FIG. 3A and FIG. 3C: DNA from virions, immunoprecipitated with monoclonal antibody to MHBs, was amplified by polymerase chain reaction (PCR) and resolved by agarose gel electrophoresis.
Figure 3B:
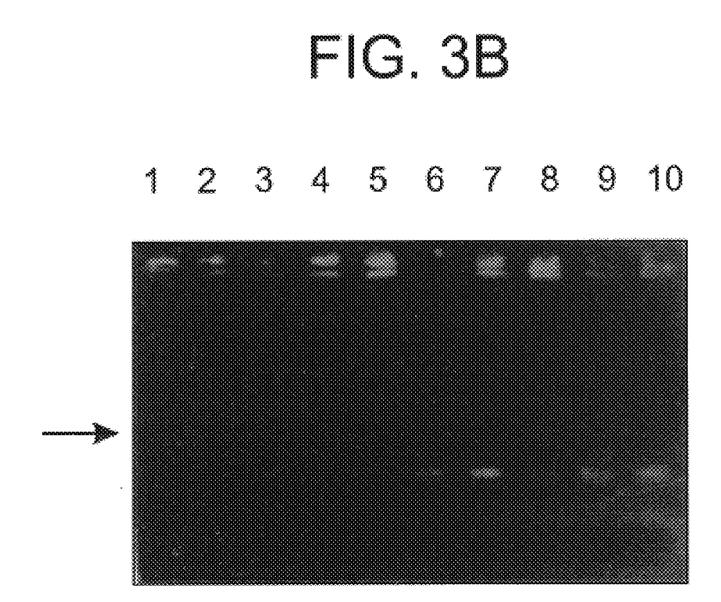
Figure 3C:
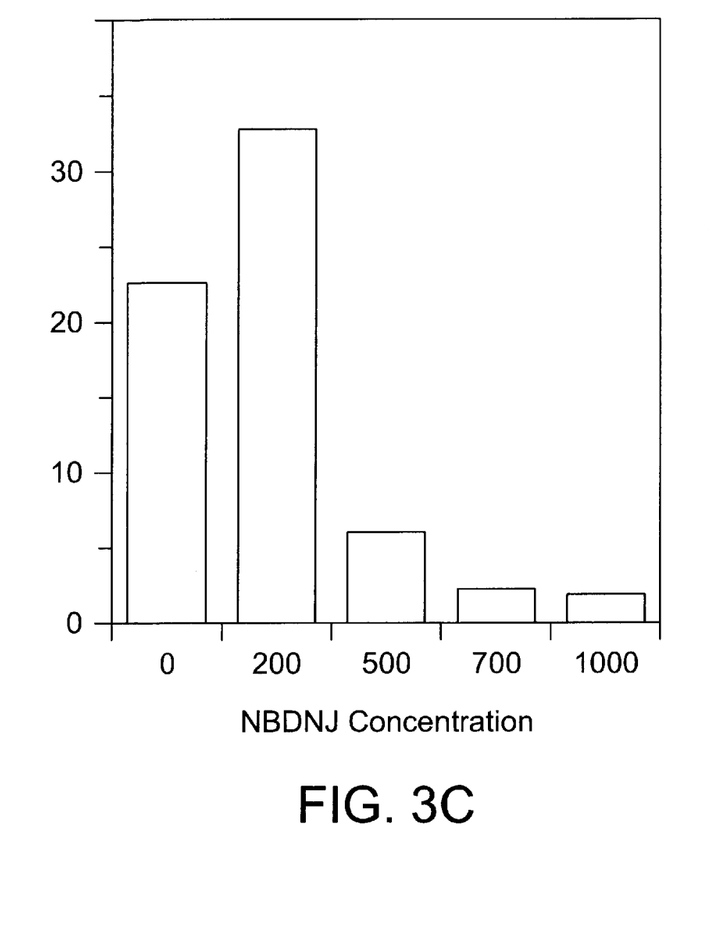

Therefore, HepG2 cells were infected with protease-modified HBV. The next day, culture medium was replaced with either control medium or medium containing various concentrations of NBDNJ. Five days after infection, progeny virions were immunoprecipitated with monoclonal antibody specific for the central portion of the PreS2 domain. HBV specific DNA sequences were amplified by PCR using HBV specific primers. Products of the reaction were resolved by agarose gel electrophoresis and imaged after ethidium bromide staining (FIG. 3A). The 519 base pair products (arrow, FIG. 3A) were quantified by densitometry analysis and the plot is shown in FIG. 3C. Although PCR may underestimate the differences between initial DNA concentrations in samples, it is evident that medium from cells infected with protease processed virus and post treated with 700 μg/ml (3.2 mM) NBDNJ contain an order of magnitude less viral DNA than do untreated samples. These results show that the NBDNJ mediated decrease in HBV released into the media is not peculiar to the 2.2.15 transfected cell system.

HepG2 cells infected with HBV and treated with NBDNJ contain increased amounts of intracellular HBV DNA.

Figure 3D:
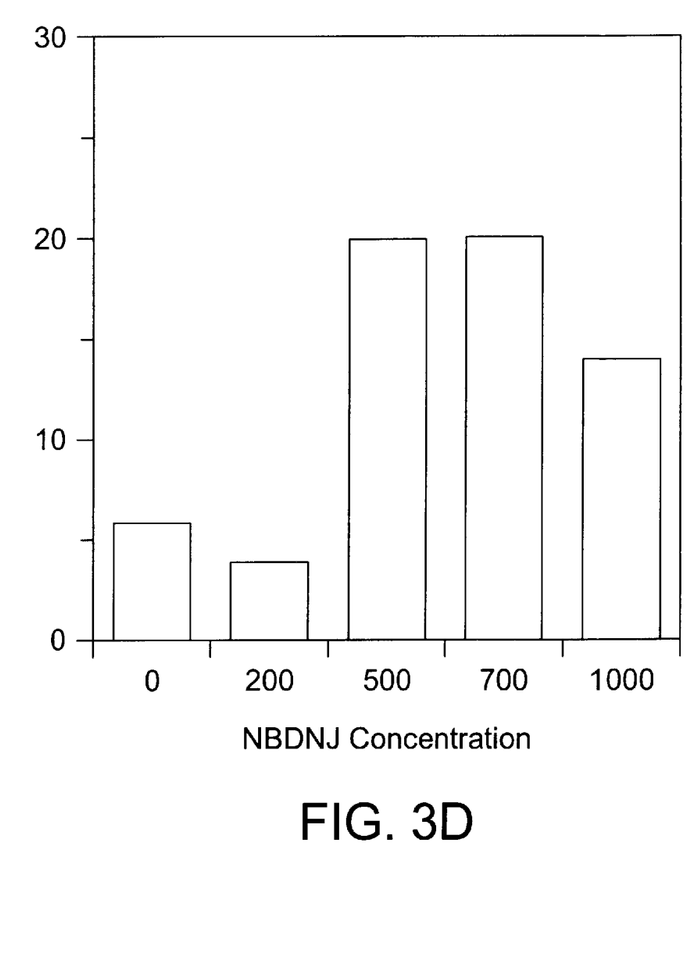
FIG. 3D: Histogram of the area under the averaged peaks of the densitometric tracing of the gel in FIG. 3B.

Since the culture medium of HBV infected HepG2 cells treated with NBDNJ was similar to 2.2.15 cells, with respect to the reduced amount of virion associated DNA, it was of interest to know if there was a concomitant increase in viral DNA within the treated cells. Total cellular DNA was prepared from samples corresponding to those presented in FIGS. 3A and C. Intracellular HBV specific DNA was amplified using PCR. Products of the reaction were resolved by agarose gel electrophoresis and the ethidium bromide stained gel (FIG. 3B) was analyzed by densitometry (FIG. 3D). Clearly, HepG2 cells infected with HBV and post treated with NBDNJ accumulate greater amounts of viral DNA than do untreated cells.

The culture medium of NBDNJ treated and untreated 2.2.15 cells contain similar amounts of HBV envelope antigen.

2.2.15 cells secrete virions as well as sub-viral particles [Sells et al., *J. Virol.* 62, 2836–2844 (1988)]. The NBDNJ-mediated reduction of virion-associated DNA in the culture medium could be a reflection of a generalized decrease in the secretion of all HBs containing particles. Alternatively, there may have been a selective diminution of the rare virion particle with a relative sparing of the other form(s), which are in vast excess.

Figure 4A:
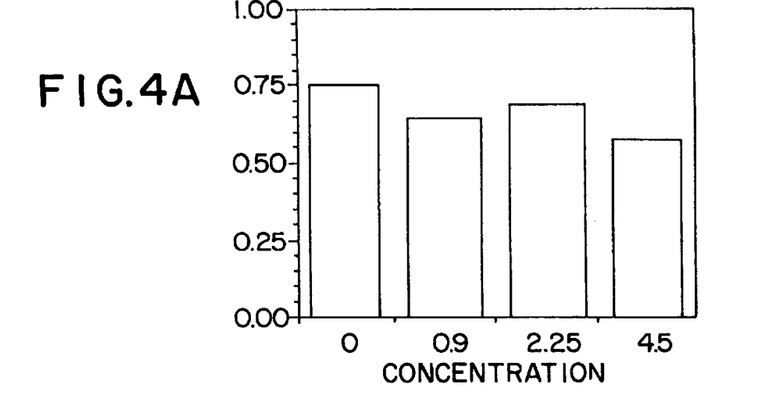
FIGS. 4A, 4B, 4C, 4D, 4E and 4F, shows HBV antigens present in the unfractionated culture medium and partially purified virion preparations. Equal volumes of the indicated samples were tested for HBV envelope antigens using the enzyme-linked imminosorbent assay (ELISA) method. Samples of unfractionated medium (FIGS. 4A, 4B and 4C) or partially purified virus (FIGS. 4D, 4E and 4F) from 3-day cultures were tested for HBV SHBs ("S") (FIGS. 4A and 4D), LHBs: "PreS1" (FIGS. 4B and 4E) or MHBs "PreS2" (FIGS. 4C and 4F) epitopes. Cultures were maintained in the indicated concentrations of NBDNJ, expressed in millimolar units and shown along the X axis.
Figure 4B:
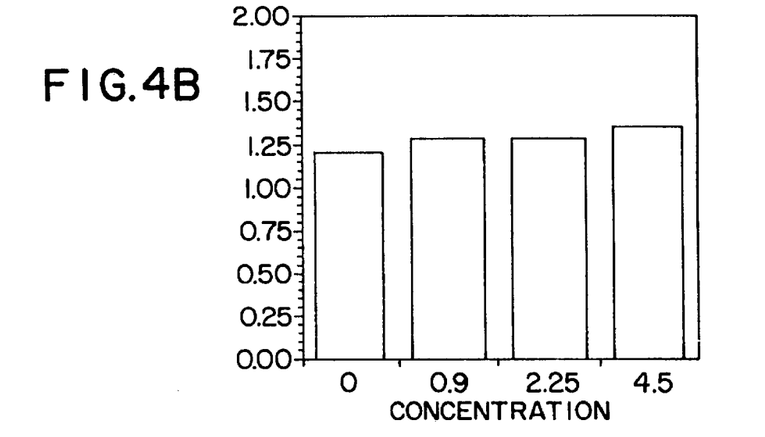
Figure 4C:
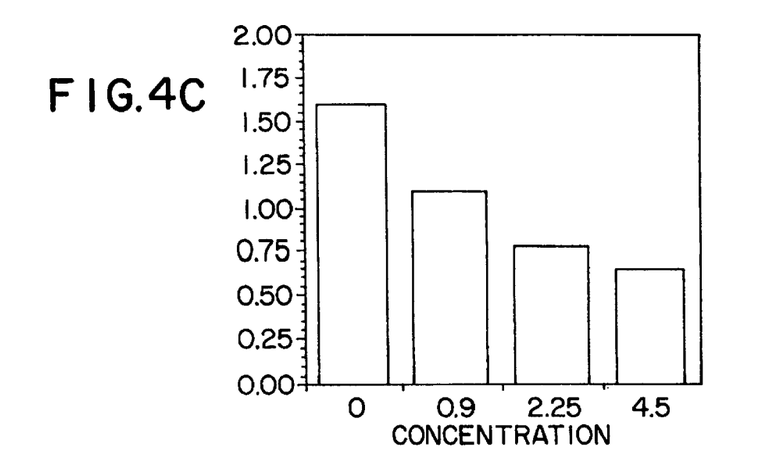
Figure 5A:
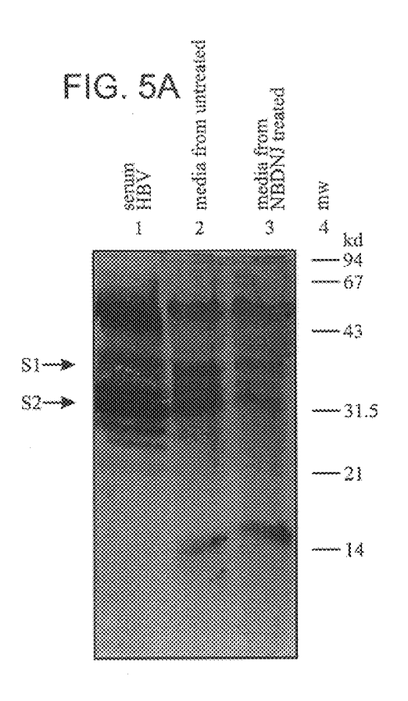
FIGS. 5A, 5B and 5C, shows Western blot analysis of LHBs and MHBs in the medium of NBDNJ treated and untreated cultures. Polyethylene glycol (PEG) precipitates of culture medium (FIG. 5A) or partly purified virions, HBs filaments and spheres from untreated (FIG. 5B) and NBDNJ treated (FIG. 5C) cultures were resolved by SDS-PAGE (13.5% acrylamide), transferred to immobilin paper and incubated with PreS1 and PreS2 specific monoclonal antibody.

To distinguish between these possibilities, the amount and nature of envelope antigens in the culture medium was determined by both ELISA and Western analysis. ELISA analysis of SHBs, MHBs and LHBs antigens present in clarified culture medium is shown in FIGS. 4A, B and C. The results show that there is no significant effect upon the total amount of SHBs (S) and LHBs (PreS1) antigens in the medium. There is a modest, dose-dependent decrease in the total amount of MHBs (PreS2) antigen in the medium. This decrease is approximately 2.5 fold at the highest NBDNJ concentration (4.5 mM or approximately 1000 μg/ml.). These results were confirmed by Western blot analysis. FIG. 5A shows Western blots of medium from control cultures and those treated with 1000 μg/ml. Here it is shown that medium from NBDNJ treated (FIG. 5A, lane 3) and untreated cultures (FIG. 5A, lane 2) contain similar amounts of MHBs (S2) and LHBs (S1) antigens.

Therefore, NBDNJ does not cause a generalized reduction in the amount of SHBs and LHBs antigens in the culture medium. There is, however, a two-fold decrease in the amount of MHBs antigen in the medium of 2.2.15 cells treated with 1000 μg/ml NBDNJ, as determined by ELISA. The culture medium of NBDNJ-treated 2.2.15 cells contains reduced amounts of HBV envelope antigens sedimenting as intact virions.

Figure 4D:
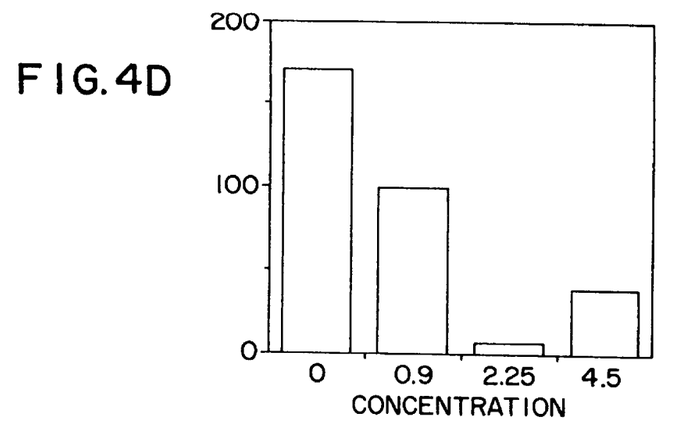
Figure 4E:
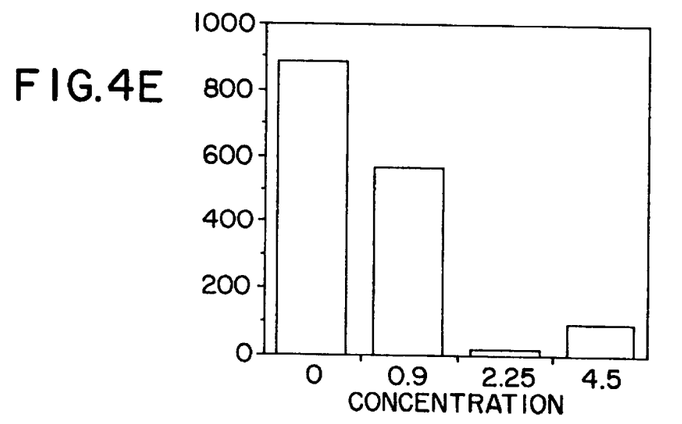
Figure 4F:
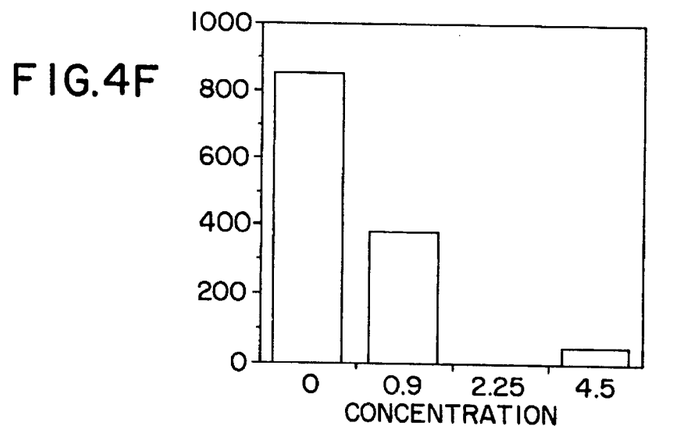

To determine the amount of HBs present in intact virions, medium from the indicated cultures was fractionated through sucrose gradients by ultracentrifugation. Secreted virions derived from treated and untreated cultures and sedimenting to 40–46% sucrose were concentrated and tested for HBs proteins by ELISA. FIGS. 4D, 4E and 4F show the results. All forms of HBs were easily detectable in samples containing virions prepared from the medium of untreated 2.2.15 cells.

On the other hand, there were virtually no detectable HBs proteins in samples prepared from the medium of cells treated with 2.25 and 4.5 mM (approximately 500 and 1000 μg/ml, respectively, for comparison) NBDNJ. This suggests a reduced amount of intact virus in the medium of these samples.

Figure 5B:
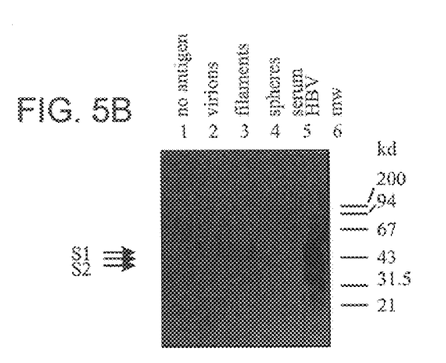
Figure 5C:
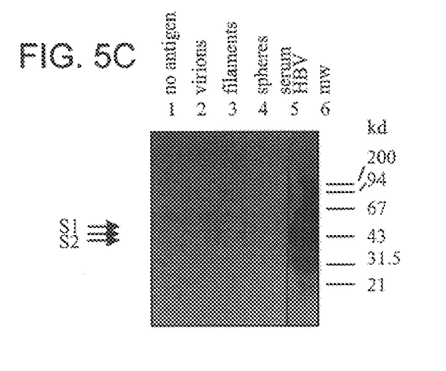

The ELISA results were confirmed by Western blot analysis of fractions from the sucrose gradient containing either intact virus, filaments or spheres (FIGS. 5B, from untreated cultures, and 5C, from NBDNJ treated cultures). Equal volumes from fractions of the sucrose gradient were resolved by SDS gel electrophoresis, transferred to membranes, incubated with antibody specific for LHBs (PresS1), imaged and then further incubated with antibody specific for MHBs (PreS2) epitopes. Partially purified HBV derived from human serum is presented in lanes 5 (FIGS. 5B and 5C) as a control.

Fractions distal to the virion containing fractions (near the bottom of the gradient) were resolved in lane 1 to show specificity of the antibody. Lanes 2, 3 and 4 (FIG. 5B and FIG. 5C) contain the intact virus, HBs filament and sphere containing fractions (respectively), as defined by sedimentation in sucrose and the presence (for virions) and absence (for sub-viral particles) of viral DNA. There is a decrease in the amount of all HBs proteins present in virions, filaments and spheres prepared from the medium of NBDNJ treated cultures (compare lanes 2, 3 and 4 in FIGS. 5B and 5C). The decrease in MHBs (PreS2 epitope) is particularly severe. The images shown in FIGS. 5B and 5C) were quantified by densitometry.

Densitometry analysis revealed that the decrease of LHBs in NBDNJ treated virion samples, compared to untreated samples, was approximately 4 fold. The decrease in MHBs, in the same lanes (FIG. 5C, lane 2 compared with FIG. 5B, lane 2) was 12 fold. It is noted that the gradient used to separate the various forms of HBs protein results in fractions "enriched" for different forms. That is, the virion containing fractions are likely to also contain filaments and spheres. This may cause an underestimation of the effect of NBDNJ upon the release of virions, relative to spheres and filaments, as judged by immunological analysis.

Nevertheless, the results of the Western blot analysis are consistent with those of the ELISA, in that medium from NBDNJ treated cultures contains similar amounts of total HBs antigens but greatly reduced antigenic material in virion fractions.

The inhibitory compounds described herein also can be used for administration to patients infected with HBV by conventional means, preferably in formulations with pharmaceutically acceptable diluents and carriers. These compounds can be used in the free amine form or in their salt form. Pharmaceutically acceptable salt derivatives are illustrated, for example, by the HCl salt.

These inhibitory compounds also can be used in the form of pro-drugs such as the 6-phosphorylated derivatives described in U.S. Pat. Nos. 5,043,273 and 5,103,008, and the O-acylated derivatives such as described, e.g., in U.S. Pat. Nos. 5,003,072; 5,144,037; and 5,221,746. A preferred such derivative is 1,5-(butylimino)-1,5-dideoxy-D-glucitol, tetrabutyrate.

The amount of the active compound to be administered must be an effective amount, that is, an amount which is medically beneficial but does not present toxic effects which overweigh the advantages which accompany its use. It would be expected that the adult human daily dosage would normally range from about one to about 1000 milligrams of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Pa., U.S.A.

Various other examples will be apparent to the person skilled in the art after reading the present disclosure without departing from the spirit and scope of the invention. It is intended that all such other examples be included within the scope of the appended claims.

What is claimed is:

1. A method for the treatment of hepatitis B virus infections in an infected human host comprising administering to said host an N-alkyl derivative of 1,5-dideoxy-1,5-imino-D-glucitol in which said alkyl group contains from 3 to 6 carbon atoms in an effective amount to inhibit replication and secretion of hepatitis B virus virions.

2. The method of claim 1 in which the alkyl group is butyl.

3. The method of claim 1 in which the effective inhibitory amount is from about one to about 1000 mg.

* * * * *